United States Patent [19]

Harada et al.

[11] 4,290,910
[45] Sep. 22, 1981

[54] FATTY EMULSION AND PROCESS FOR THE PREPARATION THEREOF

[75] Inventors: Kiyoshi Harada, Kyoto; Yoshiyuki Koida, Katano; Hiroshi Miura, Takatuki, all of Japan

[73] Assignee: Tanabe Seiyaku Co., Ltd., Osaka, Japan

[21] Appl. No.: 71,041

[22] Filed: Aug. 30, 1979

[30] Foreign Application Priority Data

Sep. 8, 1978 [JP] Japan ................... 53/111089

[51] Int. Cl.$^3$ ............................................. B01J 13/00
[52] U.S. Cl. ..................... 252/312; 252/314; 424/172; 426/602; 426/605
[58] Field of Search ................. 252/312; 426/602, 605

[56] References Cited

U.S. PATENT DOCUMENTS

| | | | |
|---|---|---|---|
| 2,628,930 | 2/1953 | Zentner | 252/356 X |
| 2,870,201 | 1/1959 | Pollack | 252/356 X |
| 2,919,197 | 12/1959 | Duin et al. | 252/308 |
| 3,533,802 | 10/1970 | Cooper et al. | 252/312 X |

FOREIGN PATENT DOCUMENTS

| | | | |
|---|---|---|---|
| 637742 | 5/1950 | United Kingdom | 252/312 |
| 667742 | 3/1952 | United Kingdom | 252/312 |

*Primary Examiner*—Richard D. Lovering
*Attorney, Agent, or Firm*—Bierman & Bierman

[57] ABSTRACT

A stable, oil-in-water type, fine particle, fatty emulsion which is regulated with a pH value regulator consisting of an organic amine and a buffer solution to a pH value of 6.0 to 8.0, said fatty emulsion having a fatty particle size of not larger than 2μ. The fatty emulsion can stably be kept for a long period of time without lowering of the pH value and aggregation of the fatty particles.

24 Claims, No Drawings

FATTY EMULSION AND PROCESS FOR THE PREPARATION THEREOF

The present invention relates to a fatty emulsion and a process for the preparation thereof. More particularly, it relates to a stable oil-in-water type fatty emulsion and a process for the preparation thereof.

Fatty emulsions are usually administered in intravenous route as a nutrient together with hydrocarbon transfusion liquid and amino acid transfusion liquid, when patients cannot take nutrients in oral or tubal route before or after operation, or when patients cannot take sufficient nutrients during a long medical treatment, or in case of emergency.

Fatty emulsions are usually prepared by emulsifying purified vegetable oils such as soy bean oil, peanut oil, cotton seed oil, sesame oil or olive oil into water, wherein the oils are contained in the form of oil-in-water type fine particles. It has been reported that acidic transfusion liquid may possibly cause phlebitis [Medical Postgraduates, Vol. 10, page 39 (1972)]. When the pH value of fatty emulsions is increased with an inorganic base such as sodium hydroxide, however, the emulsions return to an acidic pH value or the fatty particles aggregate and become coarse by sterilization treatment thereof with heating or during storage.

In order to eliminate the drawbacks of the conventional fatty emulsions, the present inventors have intensively studied. As a result, it has unexpectedly been found that when the pH value of the fatty emulsions is regulated with a combination of an organic amine and a buffer solution, the pH value is not lowered or the fatty particles do not become coarse even by the heat sterilization thereof or during storage and they can keep a fatty particle size of not larger than $2\mu$.

An object of the present invention is to provide a stable oil-in-water type fatty emulsion. Another object of the invention is to provide a fatty emulsion which pH value is regulated with a pH value regulator consisting of a combination of an organic amine and a buffer solution. These and other objects of the invention will be apparent from the following description.

The stable oil-in-water type fatty emulsion of the present invention is prepared by adding a pH value regulator consisting of a combination of an organic amine and a buffer solution to an oil-in-water type fatty emulsion.

One component of the pH value regulator is an organic amine such as lysine, arginine, ornithine, histidine, tris-hydroxymethylaminomethane, an alkanolamine of 2 to 6 carbon atoms (e.g. monoethanolamine, diethanolamine, or triethanolamine), or the like. Another component is a buffer solution such as phosphate buffer solutions (e.g. potassium dihydrogen phosphate-dipotassium hydrogen phosphate buffer solution, potassium dihydrogen phosphate-disodium hydrogen phosphate buffer solution, potassium dihydrogen phosphate-trisodium phosphate buffer solution, or sodium dihydrogen phosphate-disodium hydrogen phosphate buffer solution), citric acid-phosphate buffer solutions (e.g. citric acid-disodium phosphate buffer solution), tris-HCl buffer solution, or the like. These buffer solutions have a pH value of about 6.5 to 9.0. Suitable examples of the pH value regulator are a combination of at least one organic amine selected from lysine, arginine, trishydroxymethylaminomethane and triethanolamine and at least one buffer solution as mentioned above, which can give the desired pH value and fatty particle size.

The oil-in-water type, fine particle, fatty emulsion of the present invention comprises fats and oils, an emulsifying agent, a pH value regulator and water, wherein the fatty particles have a particle size of not larger than $2\mu$.

The fats and oils include vegetable oils, such as soy bean oil, sesame oil, peanut oil, olive oil, cotton seed oil, or the like. The emulsifying agent includes natural surfactants such as soy bean phospholipids, egg yolk phospholipids, or synthetic surfactants such as polyoxyethylene-hydrogenated castor oil. Suitable fatty emulsion is prepared by using soy bean oil as the vegetable oil and soy bean phospholipids or egg yolk phospholipids as the emulsifying agent.

Particularly suitable fatty emulsion of the present invention comprises about 3 to 30 W/V %, more preferably 5 to 20 W/V %, of a vegetable oil, about 0.3 to 5.0 W/V %, more preferably 0.7 to 1.5 W/V %, (0.5 to 20% by weight, more preferably 5 to 15% by weight based upon the vegetable oil) of an emulsifying agent, about 0.001 to 0.05 W/V % of an organic amine, about 0.005 to 4.0 mM, more preferably 0.1 to 2.0 mM, of a buffer solution, and remainder (total 100) of water, which has a pH value of about 6.0 to 8.0, more preferably 7.0 to 7.5.

The fatty emulsion of the present invention may optionally contain about 2 to 5 W/V % of an isotonic agent such as sorbitol, xylitol, glycerin or the like.

The fatty emulsion may be prepared by firstly emulsifying a vegetable oil in a dispersion of an emulsifying agent in water to give a crude emulsion, adding a pH value regulator consisting of an organic amine and a buffer solution to the crude emulsion, and then emulsifying completely the mixture; or by further emulsifying the above crude emulsion, and adding thereto the pH value regulator.

The crude emulsion may be prepared by emulsifying a vegetable oil into an aqueous dispersion of an emulsifying agent by a conventional method, for example, mixing the aqueous dispersion of an emulsifying agent and the vegetable oil in the ratio as mentioned above, and agitating vigorously the mixture at room temperature under atmospheric pressure. The crude emulsion may further emulsified, for example, by a conventional fine particle emulsifying method under a high pressure, by which there can be prepared a fatty emulsion having a fatty particle size of not larger than $2\mu$. The emulsifying method under a high pressure may be carried out under a pressure of about 50 to 500 kg/cm$^2$ for about 5 to 20 times.

In order to regulate the pH value of the emulsion, the organic amine and buffer solution may be added to the emulsion simultaneously or separately, or the organic amine and buffer solution are previously mixed and the mixture may added to the emulsion. These organic amine and buffer solution are added in an amount of about 0.001 to 0.05 W/V %, preferably 0.002 to 0.02 W/V %, and about 0.05 to 4.0 mM, preferably 0.1 to 2.0 mM, respectively, so as to regulate the pH value of the emulsion to about 6.0 to 8.0, preferably 7.0 to 7.5. The fatty emulsion thus obtained is an oil-in-water type, fine particle, fatty emulsion having a pH value of about 6.0 to 8.0 and a fatty particle size of not larger than about $2\mu$, which can be used for the intraveneous administration as it is or after being diluted with water, followed by sterilization with heating.

According to the present invention, since the pH value of the fatty emulsion is regulated with a combination of an organic amine and a buffer solution, the pH value is not decreased by the heat sterilization or during storage as is observed in case of regulation of pH value with an inorganic base, and further, the fine fatty particle size can stably be kept for a long period of time of 2 years or more without aggregation and becoming coarse.

As is clear from the following experiments, when an organic amine is used alone, the fatty particles do not aggregate but the pH value is decreased, and when a buffer solution is used alone, the pH value is decreased or the fatty particles aggregate and become coarse.

EXPERIMENT 1

(1) Preparation of test emulsion (i) Egg yolk phospholipid (240 g) was added to water (6500 ml) and the mixture was dispersed with a homomixer. To the dispersion was added soy bean oil (2000 g), and the mixture was homogenized with a homomixer to give a crude emulsion. To the crude emulsion was added water so as to become totally 10 liters. The mixture was emulsified with a high pressure emulsifier (Model 15 M, made by Manton-Gaurine Co.) under a pressure of 400 kg/cm$^2$ for 20 times to give a fatty emulsion having a fatty particle size of not larger than 2μ (10 liters).

(ii) To the fatty emulsion obtained above (100 ml) were added water (about 70 ml) and a pH value regulator as shown in Table 1 to regulate the pH value to 7.3, and thereto was further added water to give a fatty emulsion (200 ml).

(2) Method of experiment and results

The fatty emulsion (100 ml) prepared above was sterilized by heating at 121° C. for 20 minutes, and thereafter, the pH value was measured, and further the fatty particle size was observed with a microscope. The results are shown in Table 1.

TABLE 1

| pH value regulator added | pH value of fatty emulsion Before sterilization | pH value of fatty emulsion After sterilization | Observation with microscope Before sterilization | Observation with microscope After sterilization |
| --- | --- | --- | --- | --- |
| Inorganic base | | | | |
| Sodium hydroxide | 7.30 | 6.06 | No fatty particle >2 μ was observed | Fatty particles of 3–4 μ were observed. |
| Disodium hydrogen phosphate | " | 6.96 | | |
| Organic amine | | | | |
| Trishydroxyoxymethylaminomethane | 7.30 | 6.98 | No fatty particle >2 μ was observed | |
| Triethanolamine | " | 6.92 | | |
| Arginine | " | 6.53 | | |
| Lysine | " | 6.45 | | |
| Buffer solution | | | | |
| A | 7.30 | 7.24 | No fatty particle | Fatty particles |

TABLE 1-continued

| pH value regulator added | pH value of fatty emulsion Before sterilization | pH value of fatty emulsion After sterilization | Observation with microscope Before sterilization | Observation with microscope After sterilization |
| --- | --- | --- | --- | --- |
| B | " | 7.25 | ticle >2 μ was observed | ticles of 5–10 μ were observed. |
| C | " | 7.23 | | |
| D | " | 7.31 | | |
| E | " | 7.20 | | |
| — | 5.2 | 4.19 | No fatty particle >2 μ was observed | |

[Remarks]:
The buffer solutions A, B, C, D and E mean as follows:
A 1/20 M potassium dihydrogen phosphate-dipotassium hydrogen phosphate buffer solution (pH 7.4)
B 1/20 M potassium dihydrogen phosphate-disodium hydrogen phosphate buffer solution (pH 7.4)
C 1/20 M potassium dihydrogen phosphate-trisodium phosphate buffer solution (pH 7.4)
D 1/20 M citric acid-disodium hydrogen phosphate buffer solution (pH 7.4)
E 1/20 M tris-HCl buffer solution (pH 7.4)

As is clear from the above experimental results, when the pH value was regulated with the inorganic base such as sodium hydroxide and disodium hydrogen phosphate, the pH value was decreased and the fatty particles aggregated and became coarse by heat sterilization treatment. When the organic amines such as trishydroxymethylaminomethane, triethanolamine and arginine were used alone, the fatty particles did not aggregate but the pH value was decreased. Besides, when the buffer solutions were used alone in an amount that the pH value was not decreased, the fatty particles aggregated and became coarse.

EXPERIMENTS 2

(1) Preparation of test emulsion (i) To the fatty emulsion (100 ml) as obtained in Experiment 1, (1), (i) were added water (about 80 ml) and an organic amine as shown in Table 2 to regulate the pH value to 7.4, and thereto was further added water to give a fatty emulsion (200 ml).

(ii) To the fatty emulsion (100 ml) as obtained in Experiment 1, (1), (i) were added water (about 80 ml) and an organic amine and a buffer solution as shown in Table 2 to regulate the pH value to 7.4, and thereto was further added water to give a fatty emulsion (200 ml).

(iii) To the fatty emulsion (100 ml) as obtained in Experiment 1, (1), (i) were added water (about 80 ml) and a buffer solution as shown in Table 2 to regulate the pH value to 7.4, and thereto was further added water to give a fatty emulsion (200 ml).

(2) Method of experiment and results

The fatty emulsion (100 ml) prepared above was sterilized by heating at 121° C. for 20 minutes, and thereafter, the pH value was measured, and further the fatty particle size was observed with a microscope. The results are shown in Table 2.

TABLE 2

| pH value regulator | | | | pH value of fatty emulsion | | Observation with microscope |
| --- | --- | --- | --- | --- | --- | --- |
| Organic amine | | Buffer solution | | | | |
| Kind | Amount (W/V %) | Kind* | Amount (mM) | Before sterilization | After sterilization | Before and after sterilization |
| The present invention | | | | | | |
| Trishydroxymethylaminomethane Triethanol- | 0.0055 | B | 2 | | 7.28 | |

TABLE 2-continued

| pH value regulator | | | | pH value of fatty emulsion | | Observation with microscope |
|---|---|---|---|---|---|---|
| Organic amine | | Buffer solution | | | | |
| Kind | Amouunt (W/V %) | Kind* | Amount (mM) | Before sterilization | After sterilization | Before and after sterilization |
| amine | 0.0075 | B | 2 | | 7.26 | |
| Lysine | 0.0050 | B | 2 | | 7.25 | No fatty par- |
| Arginine | 0.0063 | B | 2 | 7.40 | 7.27 | ticle >2 μ |
| Arginine | 0.0063 | A | 2 | | 7.14 | was observed. |
| Arginine | 0.0063 | C | 2 | | 7.13 | |
| Arginine | 0.0063 | D | 2 | | 7.26 | |
| Arginine | 0.0063 | E | 2 | | 7.25 | |
| Reference | | | | | | |
| Arginine | 0.00625 | — | — | | 6.50 | |
| — | — | A | 2 | | 6.37 | No fatty par- |
| — | — | B | 2 | | 6.88 | ticle >2 μ |
| — | — | C | 2 | 7.40 | 6.70 | was observed. |
| — | — | D | 2 | | 6.75 | |
| — | — | E | 2 | | 6.37 | |

[Remarks]:
*The buffer solutions A, B, C, D and E mean the same as mentioned in Table 1.

As is clear from the above experimental results, when the pH value was regulated with the organic amines, the fatty particles did not aggregate but the pH value was decreased, and when the buffer solutions were used alone in an amount that the fatty particles did not aggregate, the pH value was also decreased. On the other hand, when a combination of the organic amines and the buffer solutions was used for the regulation of pH value, the pH value was not decreased and further the fatty particles did not aggregate either and could stably be kept even by heat sterilization.

EXPERIMENT 3

To the fatty emulsion (100 ml) obtained in Experiment 1, (1), (i) was added trishydroxymethylaminomethane, lysine or arginine so as to regulate the pH value to 7.4, and thereto was added 1/20 M potassium dihydrogen phosphate-disodium hydrogen phosphate buffer solution (pH 7.4) so that the final concentration of the buffer solution became 2 mM, and thereto was further added water to give a fatty emulsion (200 ml). The fatty emulsion thus obtained was sterilized by heating at 121° C. for 20 minutes, and thereafter, it was kept at 5° C., during which the pH value was measured and the fatty particles were also observed with a microscope. The results are shown in Table 3.

EXAMPLE 1

In a distilled water (1.5 liter) was dissolved glycerin (50 g), and thereto was added egg yolk phospholipids (24 g). The mixture was dispersed with a homomixer. To the resulting dispersion was added soy bean oil (200 g), and the mixture was mixed with a homomixer to give a crude emulsion. Water was added to the crude emulsion so as to make totally 1990 ml. To the crude emulsion thus obtained was added trishydroxymethylaminomethane so as to regulate the pH value to about 7.4. The crude emulsion was further emulsified with a high pressure emulsifier (model 15 M, made by Manton-Gaurine Co.) under a pressure of 400 kg/cm² for 20 times. To the resulting emulsion was added 0.1 M potassium dihydrogen phosphate-disodium hydrogen phosphate buffer solution (pH 7.4, 10 ml). After mixing well, the mixture was sterilized by heating at 121° C. for 20 minutes to give a fatty emulsion.

EXAMPLE 2

In a distilled water (1.3 liter) was dissolved sorbitol (100 g), and thereto was added soy bean phospholipid (24 g), and the mixture was mixed with a homomixer to give a crude emulsion. To the crude emulsion was added water so as to make totally 1995 ml. The crude

TABLE 3

| Fatty emulsion | pH value regulator | | pH value of fatty emulsion | | | | Observation with microscope | | | |
|---|---|---|---|---|---|---|---|---|---|---|
| | Organic amine | buffer solution | Immediately after sterilization | After six months | After one year | After two years | Immediately after sterilization | After six months | After one year | After two years |
| The present invention | Trishydroxy-methylamino-methane | B | 7.28 | 7.26 | 7.24 | 7.24 | No fatty particles >2 μ was observed. | | | |
| | Lysine | B | 7.25 | 7.25 | 7.23 | 7.21 | | | | |
| | Arginine | B | 7.27 | 7.27 | 7.25 | 7.20 | | | | |
| Reference | Arginine | — | 6.70 | 6.38 | 6.21 | 5.83 | No fatty particles >2 μ was observed. | | | |

[Remark]:
The buffer solution B means the same as defined in Table 1.

As is clear from the above experimental results, the fatty emulsion of the present invention could stably be kept for a long period of time.

Preparation of fatty emulsions of the present invention is illustrated by the following Examples but is not limited thereto.

emulsion was emulsified in the same manner as described in Example 1. To the resulting emulsion was added arginine so as to regulate the pH value to about 7.4, and thereto was added 1 M potassium dihydrogen phosphate-trisodium phosphate buffer solution (pH 7.4, 5 ml). After mixing well, the mixture was sterilized by heating at 121° C. for 20 minutes to give a fatty emulsion.

EXAMPLE 3

In a distilled water (1.3. liter) was dissolved xylitol (100 g), and thereto was added egg yolk phospholipid (24 g), and the mixture was mixed with a homomixer to give a crude emulsion. To the crude emulsion was added water so as to make totally 1990 ml. To the crude emulsion was added lysine so as to regulate the pH value to about 7.4, and thereto was added 0.2 M potassium dihydrogen phosphate-dipotassium hydrogen phosphate buffer solution (pH 7.4, 10 ml). The resulting emulsion was further emulsified with a high pressure emulsifier (Model 15 M, made by Manton-Gaurine Co.) under a pressure of 450 kg/cm$^2$ for 15 times. The mixture was sterilized by heating at 115° C. for 30 minutes to give a fatty emulsion.

We claim:

1. A fatty emulsion comprising an oil-in-water type fatty emulsion which is regulated to a pH value of 6.0 to 8.0 with a pH value regulator consisting of a combination of at least one organic amine selected from the group consisting of lysine, arginine, ornithine, histidine, trishydroxymethylaminomethane and triethanolamine and at least one buffer solution selected from the group consisting of a potassium dihydrogen phosphate-dipotassium hydrogen phosphate buffer, potassium dihydrogen phosphate-disodium hydrogen phosphate, potassium dihydrogen phosphate-trisodium phosphate, sodium dihydrogen phosphate-disodium hydrogen phosphate, citric acid-disodium hydrogen phosphate, and tris-HCl.

2. A fatty emulsion according to claim 1 wherein said organic amine is selected from the group consisting of lysine, arginine, trishydroxymethylaminomethane and triethanolamine.

3. An oil-in-water type fatty emulsion according to claim 1 comprising about 3 to 30 W/V % of a vegetable oil; about 0.3 to 5.0 W/V % of an emulsifying agent; about 0.001 to 0.05 W/V % of said organic amine, about 0.05 to 4.0 mM of said buffer solution, the remainder being water, and having a fatty particle size not larger than 2µ.

4. An oil-in-water type fatty emulsion according to claim 1, having a fatty particle size not larger than 2µ.

5. A fatty emulsion according to claim 4, wherein the emulsifying agent is selected from the group consisting of phospholipids and polyoxyethylene-hydrogenated castor oil.

6. A fatty emulsion according to claim 4, wherein the emulsifying agent is a member selected from the group consisting of soy bean phospholipids and egg yolk phospholipids.

7. A fatty emulsion according to claim 4, 5, or 6 wherein said emulsion has a pH value of about 7.0 to 7.5.

8. A fatty emulsion according to claim 4, 5, or 6 wherein the vegetable oil is soy bean oil.

9. A fatty emulsion according to claim 4, 5, or 6 wherein said regulator is a combination of trishydroxymethylaminomethane and potassium dihydrogen phosphate-disodium hydrogen phosphate.

10. A fatty emulsion according to claim 4, 5, or 6 wherein said regulator is a combination of lysine and potassium dihydrogen phosphate-disodium hydrogen phosphate.

11. A fatty emulsion according to claim 4, 5, or 6 wherein said regulator is a combination of triethanolamine and potassium dihydrogen phosphate-disodium hydrogen phosphate.

12. A fatty emulsion according to claim 4, 5, or 6 wherein said regulator is a combination of arginine and potassium dihydrogen phosphate-disodium hydrogen phosphate.

13. A fatty emulsion according to claim 4, 5 or 6 wherein said regulator is a combination of arginine and potassium dihydrogen phosphate-dipotassium hydrogen phosphate.

14. A fatty emulsion according to claim 4, 5 or 6 wherein said regulator is a combination of arginine and potassium dihydrogen phosphate-trisodium phosphate.

15. A fatty emulsion according to claim 4, 5 or 6 wherein said regulator is a combination of arginine and citric acid-disodium hydrogen phosphate.

16. A fatty emulsion according to claim 4, 5 or 6 wherein said regulator is a combination of arginine and tris-HCl.

17. A fatty emulsion according to claim 4, 5 or 6 wherein said regulator is a combination of trishydroxymethylaminomethane and citric acid-sodium hydrogen phosphate.

18. A fatty emulsion according to claim 4, 5, or 6 wherein said regulator is a combination of lysine and citric acid-disodium hydrogen phosphate.

19. A process for the preparation of a fatty emulsion which comprises emulsifying a vegetable oil into an aqueous dispersion of an emulsifying agent; adding to the resulting crude emulsion a pH value regulator consisting of at least one organic amine selected from the group consisting of lysine, arginine, ornithine, histidine, trishydroxymethylaminomethane and triethanolamine and at least one buffer selected from the group consisting of a phosphate buffer, a citric acid-phosphate buffer and tris-HCl buffer to regulate a pH value thereof to a pH range of 6.0 to 8.0; and emulsifying the mixture completely to give an oil-in-water fatty emulsion.

20. A process according to claim 19 wherein said organic amine is selected from the group consisting of lysine, arginine, trishydroxymethylaminomethane and triethanolamine.

21. A process according to claim 20 wherein said fatty emulsion comprises about 3 to 30 W/V % of said vegetable oil, about 0.3 to 5.0 W/V % of said emulsifying agent, about 0.001 to 0.05 W/V % of said organic amine, about 0.05 to 4.0 nM of said buffer solution, the remainder being water, and having a fatty particle size not larger than 2µ.

22. A process for the preparation of a fatty emulsion, which comprises emulsifying a vegetable oil into an aqueous dispersion of an emulsifying agent; emulsifying further the resulting crude emulsion to give an oil-in-water type fatty emulsion; and adding thereto a pH value regulator consisting of at least one organic amine selected from the group consisting of lysine, arginine, ornithine, histidine, trishydroxymethylaminomethane and triethanolamine and at least one buffer selected from the group consisting of a phosphate buffer, a citric acid-phosphate buffer and tris-HCl buffer to regulate a pH value thereof to a pH range of 6.0 to 8.0.

23. A process for the preparation of a fatty emulsion according to claim 22 wherein said organic amine is selected from the group consisting of lysine, arginine, trishydroxymethylaminomethane and triethanolamine.

24. A process according to claim 22, wherein said fatty emulsion comprises about 3 to 30 W/V % of said vegetable oil, about 0.3 to 5.0 W/V % of said organic amine, about 0.05 to 4.0 mM of said buffer solution, the remainder being water, and having a fatty particle size of not larger than 2µ.

* * * * *